US007773759B2

(12) United States Patent
Alves et al.

(10) Patent No.: US 7,773,759 B2
(45) Date of Patent: Aug. 10, 2010

(54) DUAL MICROPHONE NOISE REDUCTION FOR HEADSET APPLICATION

(75) Inventors: Rogerio G. Alves, Macomb Township, MI (US); Kuan-Chieh Yen, Northville, MI (US)

(73) Assignee: Cambridge Silicon Radio, Ltd., Cambridge (GB)

( * ) Notice: Subject to any disclaimer, the term of this patent is extended or adjusted under 35 U.S.C. 154(b) by 1035 days.

(21) Appl. No.: 11/502,312

(22) Filed: Aug. 10, 2006

(65) Prior Publication Data

US 2008/0037801 A1 Feb. 14, 2008

(51) Int. Cl.
*A61F 11/06* (2006.01)

(52) U.S. Cl. ................. 381/71.1; 381/66; 379/406.016; 379/406.01

(58) Field of Classification Search ......... 381/316–318, 381/320, 95, 71.6, 71.11, 71.14, 73.1, 74, 381/326, 151, 370, 375, 380, 66, 93, 83, 381/94.1, 94.2, 94.3; 370/282–286; 379/406.01–406.16; 455/570, 41.2, 41.3, 501, 63.1, 114.2
See application file for complete search history.

(56) References Cited

U.S. PATENT DOCUMENTS 5,164,984 A * 11/1992 Suhami et al. .............. 379/444
5,606,607 A * 2/1997 Yamaguchi et al. ......... 379/430
5,838,802 A * 11/1998 Swinbanks ................. 381/71.2
5,920,834 A * 7/1999 Sih et al. .................... 704/233
6,415,034 B1 * 7/2002 Hietanen .................. 381/71.6

OTHER PUBLICATIONS

Bouqui et al, "Combined Noise and Echo Reduction in Hands-Free Systems: A Survey", Nov. 30, 2001, IEEE Transactions on Speech and Audio Processing, vol. 9, No. 8, pp. 808-820.*

Gustafsson S et al. : "Combined Acoustic Echo Control and Noise Reduction for Mobile Communications", 5th European Conference on Speech Communication and Technology, Eurospeech '97. Rhodes, Greece, Sep. 22-25, 1997, European Conference On Speech Communication and Technology. (Europspeech), Grenoble: Esca, Fr., vol. 3 of 5 Sep. 22, 1997, pp. 1403-1406, XP001045084, Sec. 1.

Le Bouquin Jeannes et al. : "Combined Noise and Echo Reduction in Hands-Free Systems: A Survey" IEEE Transactions On Speech And Audio Processing, IEEE Inc. New York, US, vol. 9, No. 8, Nov. 2001, pp. 808-820, XP002335495, ISSN: 1063-6676, cited in the application Sections II, III and IV.A.

Faucon G et al. : "Echo and Noise Reduction for Hands-Free Terminals—State of the Art—", 5th European Conference On Speech Communication And Technology. Eurospeech '97. Rhodes, Greece, Sep. 22-25, 1997, European Conference on Speech Communcation and Technology (Eurospeech), Grenoble : Esca, FR, vol. 5 of 5. Sep. 22, 1997, pp. 2423-2426, XP001045184 Section 3.2.

(Continued)

*Primary Examiner*—Vivian Chin
*Assistant Examiner*—Leshui Zhang
(74) *Attorney, Agent, or Firm*—Brooks Kushman P.C.

(57) ABSTRACT

Improved vocal signals are obtained in headsets and similar devices by including a microphone inside a chamber formed at least in part by the wearer's ear. This second microphone provides a reduced noise input signal. The reduced noise signal is corrected by input from another microphone, located outside the chamber. This correction can include echo cancellation, spectral shaping, frequency extension, and the like.

24 Claims, 14 Drawing Sheets

OTHER PUBLICATIONS

Scalart P et al.: "A System for Speech Enhancement in the Context of Hands-Free Radiotelephony With Combined Noise Reduction and Acoustic Echo Cancellation" Speech Communication, Elsevier Science Publishers, Amsterdam, NL, vol. 20, No. 3-4, Dec. 1996, pp. 203-214, XP004729885, ISSN: 0167-6393, Section 5.2.

"Coupled Adaptive Filters for Acoustic Echo Control and Noise Reduction", R. Martin and J. Altenhoner, Inst.of Communication Systems and Data Processing (IND), Aachen University of Technology, Aachen, Germany, pp. 3043-3046, 1995.

* cited by examiner

DUAL MICROPHONE NOISE REDUCTION FOR HEADSET APPLICATION

BACKGROUND OF THE INVENTION

1. Field of the Invention

This invention relates to headsets used in voice communication systems.

2. Background Art

Headsets allow the wearer to send and receive vocal communications. Headsets typically include a loudspeaker or other sound generator inside or near the ear canal of the wearer and a microphone near the mouth of the wearer. The boom in wireless communications has seen an increase in the use of headsets in a wide variety of environments. This boom has been further fueled by the development of short-range wireless technology, such as Bluetooth, which allows the headphone itself to be wirelessly connected to its corresponding telecommunications device.

Increasingly, portable communication systems are being used in noisy environments such as, for example, automobiles, airports, streets, malls, restaurants, and the like. The effects of noise may increase as the headset size shrinks, moving the microphone farther away from the wearer's mouth. Noise reduction algorithms may be employed by the headset or supporting telecommunication device to reduce the effects of environmental noise. Typical noise reduction algorithms can reduce the effects of stationary noise by about 12 dB if good speech quality is to be maintained. Reducing non-stationary noise without significantly degrading voice quality is more challenging.

What is needed is to provide greater noise reduction, without sacrificing speech quality, in a voice communication headset. This improved noise reduction should be practical to implement without sacrificing other functional properties expected in portable headsets or headsets.

SUMMARY OF THE INVENTION

The present invention locates a second microphone inside a chamber formed at least in part by the wearer's ear. This second microphone provides a reduced noise input signal. The reduced noise signal is corrected by input from the first microphone, located outside the chamber. In various embodiments, this correction may include echo cancellation, spectral shaping, frequency extension, and the like.

A system is provided including an ear portion forming a chamber reducing ambient noise from outside the chamber. A first microphone, located outside the chamber, is positioned to pick up vocal sound from a wearer of the system and to generate a first signal. A speaker provides sound to the chamber. A second microphone is disposed within the chamber and generates a second signal. An echo reducer reduces the effects of the speaker signal in the second signal. A dynamic equalizer adjusts the frequency spectrum of the second signal based on the first signal to produce a filtered signal.

In an embodiment of the present invention, a first noise reducer reduces noise in the first signal.

In another embodiment of the present invention, an output signal is produced by combining low frequency output based on the filtered signal with high frequency output based on the first signal. An echo reducer may reduce the effects of a speaker signal driving the speaker in the high frequency output.

In yet another embodiment, the present invention includes a double talk detector permitting adaptation of a dynamic equalizer.

In a further embodiment of the present invention, a first analysis filter generates a first analysis filter output including a frequency domain representation of the first signal. A second analysis filter generates a second analysis filter output including a frequency domain representation of the second signal. A synthesis filter generates a time domain representation of the filtered signal.

A method of generating a reduced noise vocal signal in a system having a first microphone and an earpiece is also provided. The earpiece forms a chamber with an ear when the earpiece is in contact with the ear. The earpiece includes a speaker and a second microphone sensing sound in the chamber. Output of the first microphone is decomposed into a first subbanded signal and output of the second microphone is decomposed into a second subbanded signal. An equalized signal is generated by equalizing the second subbanded signal to the first subbanded signal. The reduced noise vocal signal is produced based on the equalized signal and on the first subbanded signal.

A method of generating a reduced noise vocal signal is also provided. The system employs a first microphone and an earpiece. The earpiece forms a chamber with an ear when the earpiece is in contact with the ear. The earpiece includes a speaker and a second microphone. Noise is filtered from the first microphone signal to produce a first filtered signal. An equalized signal is generated by equalizing the second microphone signal to the first filtered signal. Noise is filtered from the equalized signal to produce a second filtered signal. The reduced noise vocal signal is generated based on the first filtered signal and the second filtered signal.

A system for generating a reduced noise vocal signal based on speech spoken by a user is also provided. An ear portion forms a chamber with at least a portion of the user's ear. The chamber reduces ambient noise from outside the chamber. The chamber includes a speaker providing sound to the user's ear. A first microphone outside the chamber is positioned to pick up the user's speech and to generate a first signal based on the speech. The system includes a second microphone disposed within the chamber generating a second signal based on the speech spoken by the user. Audio processing circuitry generates the reduced noise vocal signal by processing the second signal based on the first signal.

DETAILED DESCRIPTION OF THE PREFERRED EMBODIMENT(S)

Figure 1:
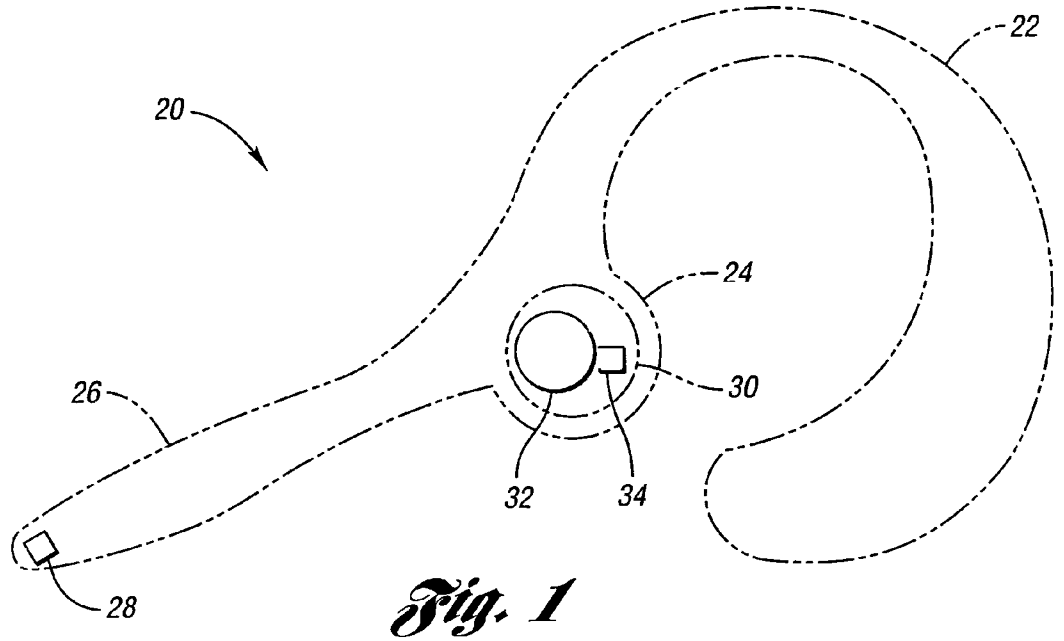
FIG. 1 is a schematic diagram of headset that incorporates a second microphone according to an embodiment of the present invention.

Referring to FIG. 1, a schematic diagram of headset that incorporates a second microphone according to an embodiment of the present invention. A headset, shown generally by 20, includes curved portion 22 which fits around the wearer's ear such that earpiece portion 24 fits within the ear. Boom portion 26 extends from earpiece 24 in the direction of the wearer's mouth. Details of curved portion 22, earpiece 24, and boom 26 are well known in the art and have been omitted from FIG. 1. Boom 26 places first microphone relative to the wearer's mouth. Earpiece 24 is formed so that insertion portion 30 fits at least partially within the ear canal of the wearer so as to form a chamber including speaker 32 and second microphone 34.

A wide variety of configurations may be used in the present invention. For example, first microphone 28 need not be rigidly or fixedly located relative to second microphone 34 such as, for example, if first microphone is located on a wire interconnecting earpiece 24 with a telecommunications device. Moreover, headset 20 may include stereo speakers 32 with second microphone 34 collocated with one or both speakers 32, the latter case including two second microphones 34. Headset 20 may be wired or wireless.

Figure 2:
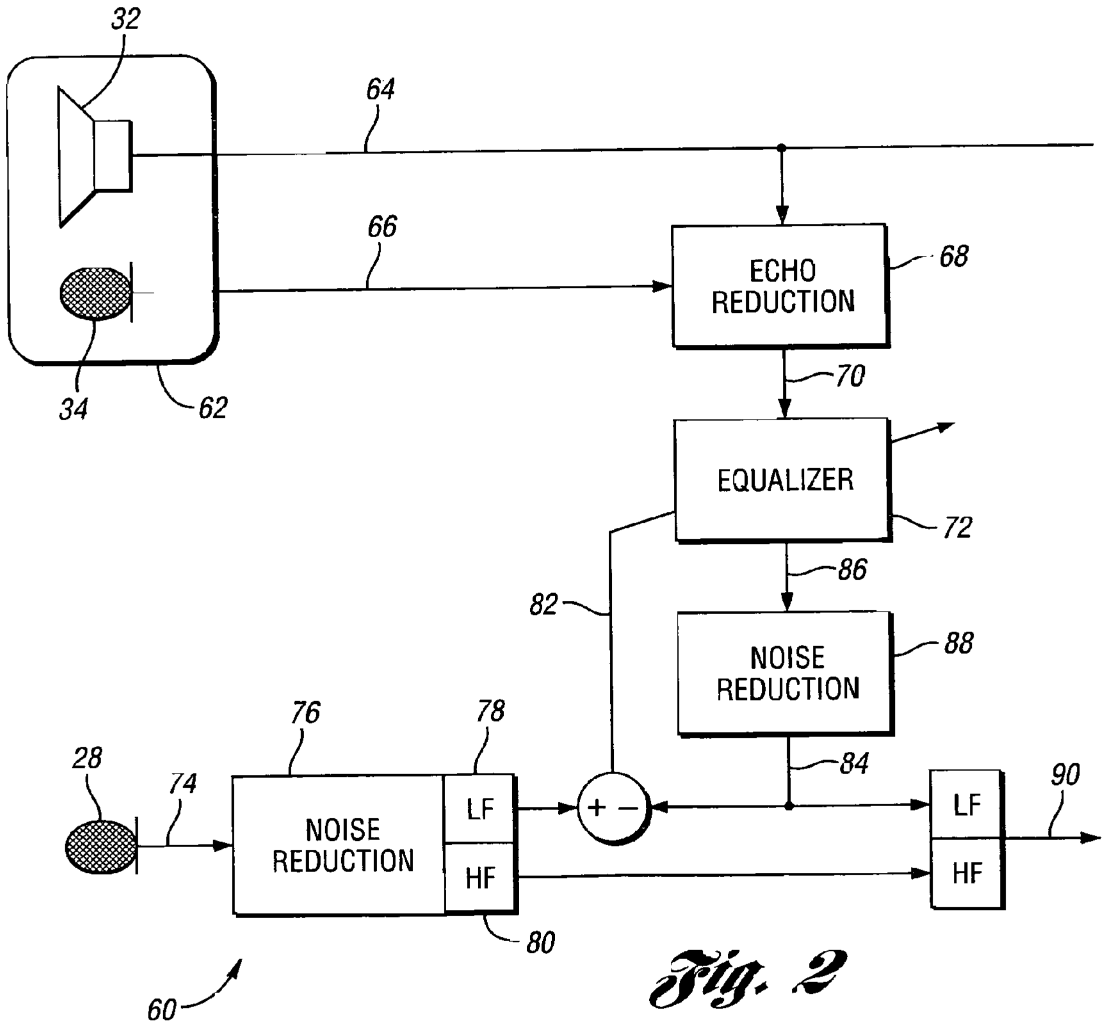
FIG. 2 is a block diagram for noise reduction according to an embodiment of the present invention.

Referring now to FIG. 2, a block diagram for noise reduction according to an embodiment of the present invention is shown. A system for generating a reduced noise vocal signal, shown generally by 60, includes first microphone 28, second microphone 34, and speaker 32. Second microphone 34 and speaker 32 are located within chamber 62 formed at least in part by the ear of the wearer or user, and typically also by a portion of the headset supporting speaker 32 and second microphone 34.

Due to its location within chamber 62, second microphone 34 will receive less noise than first microphone 28. Second microphone 34 will still receive adequate speech signal content from the wearer as sound propagating through structures in the head and into the ear canal of the wearer. Second microphone 34 with therefore typically experience a better a signal-to-noise ratio than first microphone 28. Second microphone 34 can suffer, however, from several disadvantages due to its location within chamber 62. First, second microphone 34 will pick up sound emitted by speaker 32. This sound will appear as an echo in the output of second microphone 34. In addition, the spectrum of speech received in chamber 62 is likely to have less high frequency content than the speech received by first microphone 28. This may result in an unnatural sound when a signal from second microphone 34 is reproduced as sound. Signal processing in system 60 reduces the effects of echo and high frequency reduction while maintaining reduced noise. It should be understood that not all signal processing need be present in every implementation of the present invention or, if present, need be active at all times.

Speaker 32 is driven by speaker signal 64. Second microphone 34 generates second microphone signal 66 which will include output from speaker 32 as well as desired source sound and residual noise that penetrates into chamber 62. Echo reducer 68 decreases the effects of speaker output in second microphone signal 66. Echo reducer output 70 feeds adaptive equalizer 72.

First microphone 28 generates first microphone signal 74. Noise reducer 76 may be used to eliminate some noise from first microphone signal 74. the reduced noise output of first microphone 28 is divided into low frequency first signal 78 and high frequency first signal 80. Difference signal 82 is generated as the difference between low frequency first signal 78 and noise reduced second signal 84. Difference signal 82 is used to set filter coefficients in dynamic/adaptive equalizer 72.

Adaptive equalizer 72 adjusts the output of second microphone 34 to the spectral characteristics of the speech signal received by first microphone 28, within the frequency range of interest in second microphone signal 66. The output of equalizer 72, equalized signal 86, is filtered by noise reducer 88 to produce noise reduced second signal 84. Coefficients in noise reducer 88 may be the same as the low frequency coefficients of noise reducer 76. Output signal 90 is constructed by frequency extending noise reduced second signal 84 with high frequency first signal 80.

Figure 3:
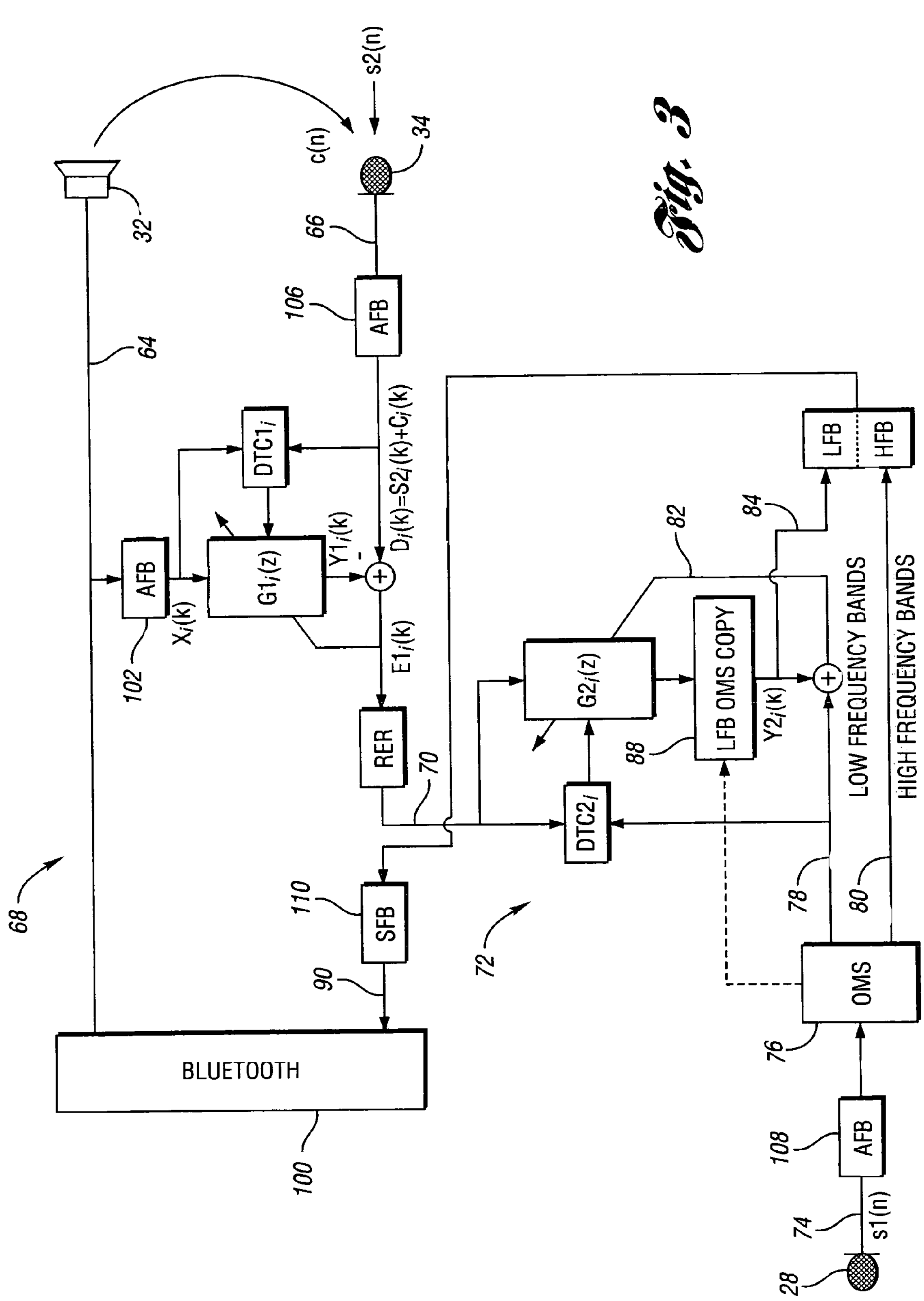
FIG. 3 is a block diagram showing further detail for noise reduction according to an embodiment of the present invention.

Referring now to FIG. 3, a block diagram showing further detail for noise reduction according to an embodiment of the present invention is shown. Bluetooth subsystem 100 provides a wireless link for receiving signals to be played through speaker 32 and for sending signals received from microphones 28, 34. Analysis filter bank (AFB) 102 generates a set of subbands, $X_i(k)$, of speaker signal 64. AFB 106 generates a set of second microphone input subbands, $D_i(k)$, for second microphone signal 66. The input to second microphone 34 is represented as having a coupled component, c(n), from speaker 32 and a signal component, $s\mathbf{2}(n)$, representing the sum of the desired sound and noise as received within the chamber at least partially enclosing second microphone 34.

Double talk controller $DTC\mathbf{1}_i$ receives both the subbanded speaker and second microphone signals, and restricts the conditions under which adaptive filters $G\mathbf{1}_i(z)$ may adapt. Adaptive filters $G\mathbf{1}_i(z)$ filter speaker subbands $X_i(k)$ to generate output $Y\mathbf{1}_i(k)$. The difference between second microphone input subbands $D_i(k)$ and filter output $Y\mathbf{1}_i(k)$ is echo canceled subbanded signal $E\mathbf{1}_i(k)$, which is used to generate filter coefficients for adaptive filters $G\mathbf{1}_i(z)$. The echo canceled subbanded signal is further processed by residual error reduction (RER) to generate echo reducer output 70.

Various embodiments for generating a reduced echo signal are disclosed in U.S. patent application Ser. No. 10/914,898 filed Aug. 10, 2004, the disclosure of which is incorporated by reference in its entirety.

AFB 108 generates a set of first microphone input subbands for first microphone signal 74, indicated as $s\mathbf{1}(n)$. These subbands are filtered to reduce noise in noise reducer 76 to produce low frequency first signal 78 and high frequency first signal 80. Echo reducer output 70 and low frequency first signal 78 are used by double talk detector $DTC\mathbf{2}_i$ to restrict conditions under which adaptive filters $G\mathbf{2}_i(z)$ may adapt. Adaptive filters $G\mathbf{2}_i(z)$ filter equalizes echo reducer output 70. The output of adaptive filters $G\mathbf{2}_i(z)$ is filtered by noise reducer 88 to produce noise reduced second signal 84, indicated as $Y\mathbf{2}_i(k)$. Coefficients in noise reducer 88 may be the same as the low frequency coefficients of noise reducer 76. SFB 110 generates output signal 90 based on high frequency first signal 80 and noise-reduced second signal 84. Output signal 90 is delivered to Bluetooth system 100 for wireless transmission.

Figure 4:
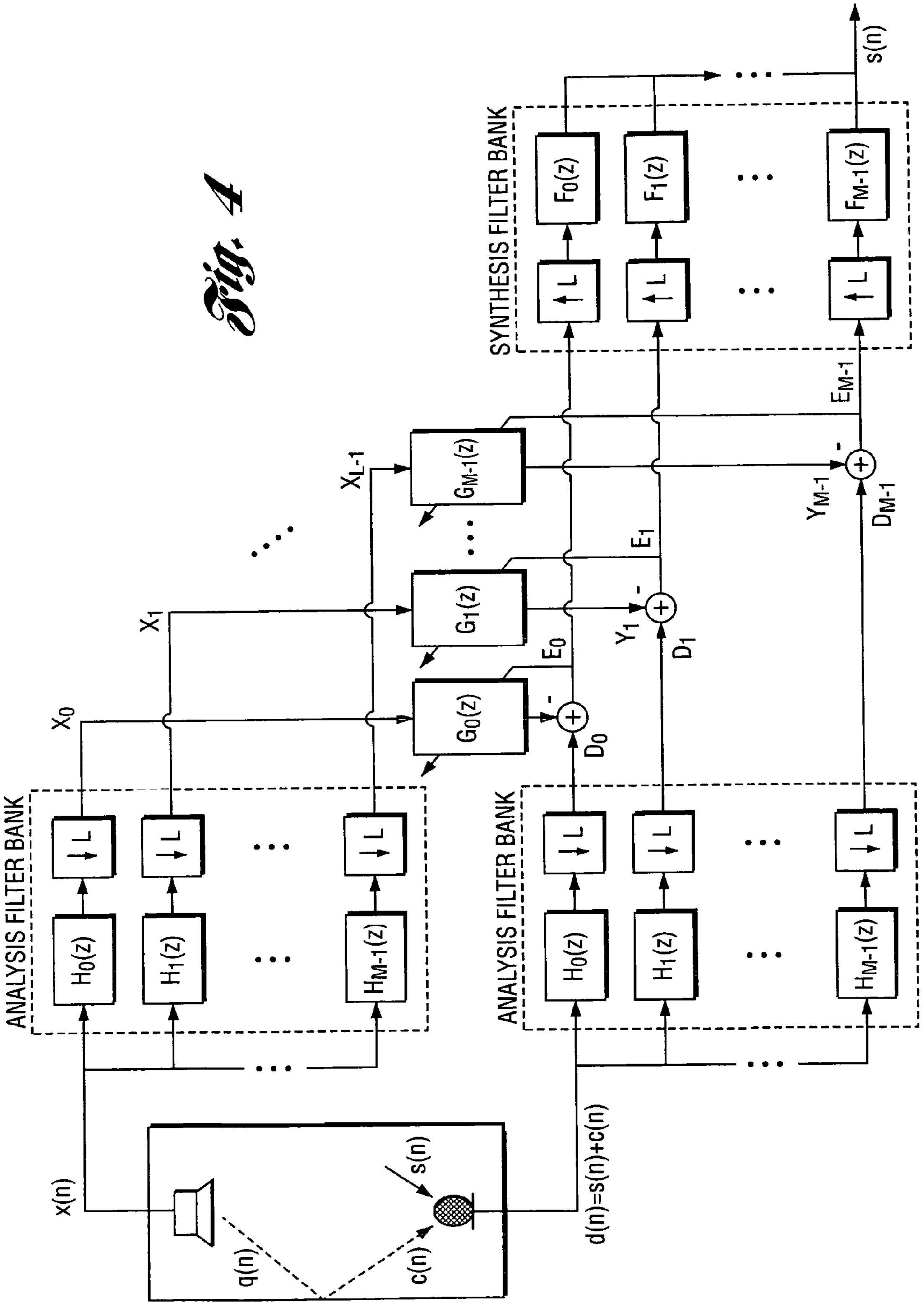
FIG. 4 is a block diagram illustrating a subband structure for an adaptive filter that may be used to implement an embodiment of the present invention.

Adaptive filters for use in the present invention may be implemented in using any of a wide variety of architectures and algorithms. Referring now to FIG. 4, a block diagram illustrating an adaptive filter that may be used to implement an embodiment of the present invention. The adaptive filter algorithm used is the second-order data reuse normalized least mean square (DR-NLMS) algorithm in the frequency domain. The subband adaptive filter structure used to implement the DR-NLMS in subbands consists of two analysis filter banks, which split the speaker signal, x(n), and microphone signal, d(n), into M bands each. The subband signals $X_i(k)$ are modified by an adaptive filter, after being decimated by a factor L, and the coefficients of each subfilter, $G_i$, are adapted independently using the individual error signal of the corresponding band, $E_i$. In order to avoid aliasing effects, this structure uses a down-sampling factor L smaller than the number of subbands M. The analysis and synthesis filter banks can be implemented by uniform DFT filter banks, so that the analysis and synthesis filters are shifted versions of the low-pass prototype filters, i.e., $$H_i(z)=H_0(zW_M^i)$$

$$F_i(z)=F_0(zW_M^i)$$

with i=0, 1, . . . , M−1, where $H_0(z)$ and $F_0(z)$ are the analysis and synthesis prototype filters, respectively, and $$W_M = e^{-j\frac{2\pi}{M}}.$$

Uniform filter banks can be efficiently implemented by the Weighted Overlap-Add (WOA) method.

The coefficient update equation for the subband structure, based on the NLMS algorithm, is given by:

$$\underline{G}_i(k+1)=\underline{G}_i(k)+\mu_i(k)[\underline{X}_i^*(k)E_i(k)]$$

where '*' represents the conjugate value of $\underline{X}_i(k)$, and:

$$E_i(k)=D_i(k)-Y_i(k)$$

$$Y_i(k)=\underline{X}_i^T(k)\underline{G}_i(k)$$

$$\mu_i(k)=\frac{\mu}{P_i(k)}$$

are the error signal, the output of the adaptive filter and the step-size in each subband, respectively.

The step size appears normalized by the power of the reference signal. The constant μ is a real value, and $P_i(k)$ is the power estimate of the reference signal $X_i(k)$, which can be obtained recursively by the equation:

$$P_i(k+1)=\beta P_i(k)+(1-\beta)|X_i(k)|^2$$

for 0<β<1.

If the system to be identified has N coefficients in fullband, each subband adaptive filter, $\underline{G}_i(k)$, will be a column vector with N/L complex coefficients, as well as $\underline{X}_i(k)$. $D_i(k)$, $X_i(k)$, $Y_i(k)$ and $E_i(k)$ are complex numbers. The choice of N is related to the tail length of the echo signal to cancel, for example, if $f_s$=8 kHz, and the desired tail length is 64 ms, N=8000×0.064=512 coefficients, for the time domain fullband adaptive filter. The value β is related to the number of coefficients of the adaptive filter ((N−L)/N). The number of subbands for real input signals is M=(Number of FFT points)/2+1.

The previous equations describe the NLMS in subband. The DR-NLMS may be obtained by computing the "new" error signal, $E_i(k)$, using the updated values of the subband adaptive filter coefficients, and to update again the coefficients of the subband adaptive filters:

$$Y_i^j(k)=\underline{X}_i^T(k)\underline{G}_i^{j-1}(k)$$

$$E_i^j(k)=D_i(k)-Y_i^j(k)$$

$$\mu_i^j(k)=\frac{\mu^j}{P_i(k)}$$

$$\underline{G}_i^j(k)=\underline{G}_i^{j-1}(k)+\mu_i^j(k)[\underline{X}(k)E_i^j(k)]$$

where j=2, . . . R represents the number of reuses that are in the algorithm, also known as order of the algorithm, and $$\underline{G}_i^1(k)=\underline{G}_i(k)\mu_i^1(k)=\mu_i(k)E_i^1(k)=E_i(k) \text{ and } Y_i^1(k)=Y_i(k).$$

Figure 5:
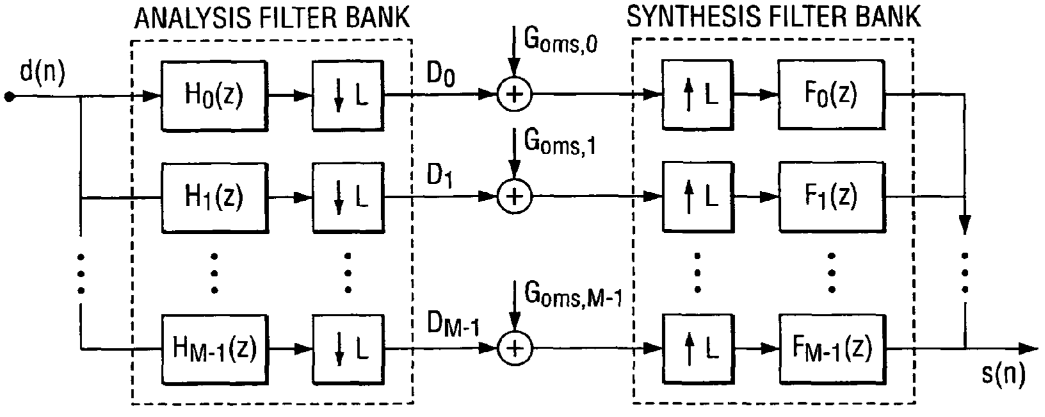
FIG. 5 is a block diagram illustrating subband noise cancellation that may be used to implement an embodiment of the present invention.

Various noise cancellation algorithms and architecture may be used to implement the present invention. Referring now to FIG. 5, a block diagram illustrating noise cancellation that may be used to implement an embodiment of the present invention is shown. The noise cancellation algorithm considers that a speech signal s(n) is corrupted by additive background noise v(n), so the resulting noisy speech signal d(n) can be expressed as $$d(n)=s(n)+v(n).$$

For the purpose of this noise cancellation algorithm, the background noise is defined as the quasi-stationary noise that varies at a much slower rate compared to the speech signal.

The noise cancellation algorithm is a frequency-domain based algorithm. With a DFT analysis filter bank with length (2M−2) DFT, the noisy signal d(n) is split into M subband signals, $D_i(k)$, i=0, 1 . . . , M−1, with the center frequencies uniformly spaced from DC to Nyquist frequency. Except the DC and the Nyquist bands (bands 0 and M−1, respectively), all other subbands have equal bandwidth which equals to 1/(M−1) of the overall effective bandwidth. In each subband, the average power of quasi-stationary background noise is tracked, and then a gain is decided accordingly and applied to the subband signals. The modified subband signals are subsequently combined by a DFT synthesis filter bank to generate the output signal. When combined with other frequency-domain modules, the DFT analysis and synthesis banks may be moved to the front and back of all modules, respectively.

Because it is assumed that the background noise varies slowly compared to the speech signal, the power in each subband can be tracked by a recursive estimator $$\begin{aligned}P_{NZ,i}(k) &= (1-\alpha_{NZ})P_{NZ,i}(k-1)+\alpha_{NZ}|D_i(k)|^2\\ &= P_{NZ,i}(k-1)+\alpha_{NZ}(|D_i(k)|^2-P_{NZ,i}(k-1))\end{aligned}$$

where the parameter $\alpha_{NZ}$ is a constant between 0 and 1 that decides the weight of each frame, and hence the effective average time. The problem with this estimation is that it also includes the power of speech signal in the average. If the speech is not sporadic, significant over-estimation can result. To avoid this problem, a probability model of the background noise power may be used to evaluate the likelihood that the current frame has no speech power in the subband. When the likelihood is low, the time constant $\alpha_{NZ}$ is reduced to drop the influence of the current frame in the power estimate. The likelihood is computed based on the current input power and the latest noise power estimate:

$$L_{NZ,i}(k)=\frac{|D_i(k)|^2}{P_{NZ,i}(k-1)}\exp\left(1-\frac{|D_i(k)|^2}{P_{NZ,i}(k-1)}\right)$$

and the noise power is estimated as $$P_{NZ,i}(k)=P_{NZ,i}(k-1)+(\alpha_{NZ}L_{NZ,i}(k))(|D_i(k)|^2-P_{NZ,i}(k-1)).$$

The value of $L_{NZ,i}(k)$ is between 0 and 1; reaches 1 only when $|D_i(k)|^2$ is equal to $P_{NZ,i}(k-1)$; and reduces towards 0 when $|D_i(k)|^2$ and $P_{NZ,i}(k-1)$ diverge. This allows smooth transitions to be tracked but prevents any dramatic variation from affecting the noise estimate.

In practice, less constrained estimates are computed to serve as the upper- and lower-bounds of $P_{NZ,i}(k)$. When it is detected that $P_{NZ,i}(k)$ is no longer within the region defined by the bounds, $P_{NZ,i}(k)$ is adjusted according to these bounds and the adaptation continues. This enhances the ability of the algorithm to accommodate occasional sudden noise floor changes, or to prevent the noise power estimate from being trapped due to inconsistent audio input stream.

Typically, the speech signal and the background noise are independent, and thus the power of the microphone signal is equal to the power of the speech signal plus the power of background noise in each subband. The power of the microphone signal can be computed as $|D_i(k)|^2$. With the noise power available, an estimate of the speech power is $$P_{SP,i}(k)=\max(|D_i(k)|^2-P_{NZ,i}(k),0)$$

and therefore, the optimal Wiener filter gain can be computed as $$G_{T,i}(k)=\max\left(1-\frac{P_{NZ,i}(k)}{|D_i(k)|^2},0\right).$$

However, since the background noise is a random process, the exact background noise power at any given time fluctuates around an average power even if the noise is stationary. By simply removing the average noise power, a noise floor with quick variations is generated, which is often referred to as musical noise or watery noise. This is a problem with algorithms based on spectral subtraction. Therefore, the instantaneous gain $G_{T,i}(k)$ needs to be further processed before being applied.

When $|D_i(k)|^2$ is much larger than $P_{NZ,i}(k)$, the fluctuation of noise power is minor compared to $|D_i(k)|^2$, and hence $G_{T,i}(k)$ is very reliable. On the other hand, when $|D_i(k)|^2$ approximates $P_{NZ,i}(k)$, the fluctuation of noise power becomes significant, and hence $G_{T,i}(k)$ varies quickly and is unreliable. In accordance with an aspect of the invention, more averaging is necessary in this case to improve the reliability of gain factor. To achieve the same normalized variation for the gain factor, the average rate needs to be proportional to the square of the gain. Therefore the gain factor $G_{oms,i}(k)$ is computed by smoothing $G_{T,i}(k)$ with the following algorithm:

$$G_{oms,i}(k)=G_{oms,i}(k-1)+(\alpha_G G_{0,i}^2(k)(G_{T,i}(k)-G_{oms,i}(k-1))$$

$$G_{0,i}(k)=G_{oms,i}(k-1)+0.25\times(G_{T,i}(k)-G_{oms,i}(k-1))$$

where $\alpha_G$ is a time constant between 0 and 1, and $G_{0,i}(k)$ is a pre-estimate of $G_{oms,i}(k)$ based on the latest gain estimate and the instantaneous gain. The output signal can be computed as $$\hat{S}_i(k)=G_{oms,i}(k)\times D_i(k).$$

The value of $G_{oms,i}(k)$ is averaged over a long time when it is close to 0, but is averaged over a shorter time when it approximates 1. This creates a smooth noise floor while avoiding generating ambient speech.

Double-talk control for use in the present invention may be implemented in using any of a wide variety of architectures and algorithms. The signal from second microphone 34, represented here as d(n), can be decomposed as $$d(n)=d_{ne}(n)+d_{fe}(n)$$

where the near-end component $d_{ne}(n)$ is the sum of the near-end speech s(n) and background noise v(n), and the far-end or speaker component $d_{fe}(n)$ is the acoustic echo, which is the speaker signal modified by the acoustic path: $c(n)=q(n)\otimes x(n)$. The NLMS filter estimates the acoustic path by matching the speaker signal, x(n), to the microphone signal, d(n), through correlation. If both near-end speech and background noise are uncorrelated to the reference signal, the adaptive filter should converge to the acoustic path, q(n).

However, since the NLMS is a gradient-based adaptive algorithm that approximates the actual gradients by single samples, the filter coefficients drift around the ideal solutions even after the filter converges. The range of drifting, or misadjustment, depends mainly on two factors: adaptation gain constant $\mu$ and the energy ratio between near-end and far-end components.

The misadjustment affects acoustic echo cancellation (AEC) performance. When near-end speech or background noise is present, this increases the near-end to far-end ratio, and hence increases the misadjustment. Thus the filter coefficients drift further away from the ideal solution, and the residual echo becomes louder as a result. This problem is usually referred to as divergence.

Traditional AEC algorithms deal with the divergence problem by deploying a state machine that categorizes the current event into one of four categories: silence (neither far-end nor near-end speech present), receive-only (only far-end speech present), send-only (only near-end speech present), and double-talk (both far-end and near-end speech present). By adapting filter coefficients during the receive-only state and halting adaptation otherwise, the traditional AEC algorithm prevents divergence due to the increase in near-end to far-end ratio. Because the state machine is based on the detection of voice activities at both ends, this method is often referred to as double-talk detection (DTD).

Although working nicely in many applications, the DTD inherits two fundamental problems. First, DTD completely ignores the near-end background noise as a factor. Second, DTD only allows filter adaptation in the receive-only state, and thus cannot handle any echo path variation during other states. These problems are not significant when the background noise level is relatively small and the near-end speech is sporadic. However, when background noise becomes significant, not only does accuracy of state detection suffer but balance between dynamic tracking and divergence prevention also becomes difficult. Therefore, a great deal of tuning effort is necessary for a traditional DTD-based system, and system robustness is often a problem. Furthermore, the traditional DTD-based system often manipulates the output signal according to the detected state in order to achieve better echo reduction. This often results in half-duplex-like performance in noisy conditions.

To overcome the deficiency of the traditional DTD, a more sophisticated double-talk control (DTC) may be used in order to achieve better overall AEC performance. Since the misadjustment mainly depends on two factors, adaptation gain constant and near-end to far-end ratio, using adaptation gain constant as a counter-balance to the near-end to far-end ratio can keep the misadjustment at a constant level and thus reduce divergence. To achieve this, it is necessary that $$\mu \propto \left(\frac{\text{far-end energy}}{\text{total energy}}\right)^2 = \left(\frac{E\{|d_{fe}(n)|^2\}}{E\{|d(n)|^2\}}\right)^2.$$

When there is no near-end component, the filter adaptation proceeds at full speed. As the near-end to far-end ratio increases, the filter adaptation slows down accordingly. Finally, when there is no far-end component, the filter adaptation is halted since there is no information about the echo path available. Theoretically, this strategy achieves optimal balance between dynamic tracking ability and filter divergence control. Furthermore, because the adaptive filter in each subband is independent from the filters in other subbands, this gain control decision can be made independent in each subband and becomes more efficient.

An obstacle of this strategy is the availability of the far-end (or equivalently, near-end) component. With access to these components, there would be no need for an AEC system. Therefore, an approximate form is used in the adaptation gain control:

$$\mu_i \frac{|E\{D_i(k)Y_i^*(k)\}|^2}{E\{|D_i(k)|^2\}^2}\gamma$$

where $\gamma$ is a constant that represents the maximum adaptation gain. When the filter is reasonably close to converging, $Y_i(k)$ would approximate the far-end component in the i-th subband, and therefore, $E\{D_i(k)Y^*_i(k)\}$ would approximate the far-end energy. In practice, the energy ratio may be limited to its theoretical range bounded by 0 and 1 (inclusively). This gain control decision works effectively in most conditions, with two exceptions which will be addressed in the subsequent discussion.

From the discussion above, $E\{D_i(k)Y^*_i(k)\}$ approximates the energy of the far-end component only when the adaptive filter converges. This means that over- or under-estimation of the far-end energy can occur when the filter is far from convergence. However, increased misadjustment, or divergence, is a problem only after the filter converges, so over-estimating the far-end energy actually helps accelerating the convergence process without causing a negative trade-off. On the other hand, under-estimating the far-end energy slows down or even paralyzes the convergence process, and therefore is a concern with the aforementioned gain control decision.

Specifically, under-estimation of far-end energy happens when $E\{D_i(k)Y^*_i(k)\}$ is much smaller than the energy of far-end component, $E\{|D_{fe,i}(k)|^2\}$. Under-estimating mainly happens in the following two situations. First, when the system is reset, with all filter coefficients initialized as zero, $Y_i(k)$ would be zero. This leads to the adaptation gain $\mu$ being zero and the adaptive system being trapped as a result. Second, when the echo path gain suddenly increases, the $Y_i(k)$ computed based on the earlier samples would be much weaker than the actual far-end component. This can happen when the distance between speaker and microphone is suddenly reduced. Additionally, if the reference signal passes through an independent volume controller before reaching the speaker, the volume control gain also figures into the echo path. Therefore, turning up the volume can also increase echo path gain drastically.

For the first situation, the adaptation gain control is suspended for a short interval right after the system reset, which helps kick-start the filter adaptation. For the second situation, an auxiliary filter ($\underline{G}'_i(k)$) is introduced to relieve the under-estimation problem. The auxiliary filter is a plain subband NLMS filter, parallel to the main filter, with the number of taps sufficient to cover the main echo path. The adaptation gain constant should be small enough such that no significant divergence would result without any adaptation gain or double-talk control mechanism. After each adaptation, the 2-norms of the main and auxiliary filters in each subband are computed as:

$$SqGa_i(k)=\|\underline{G}_i(k)\|_2$$

$$SqGb_i(k)=\|\underline{G}'_i(k)\|_2$$

These are estimates of echo path gain from each filter, respectively. Since the auxiliary filter is not constrained by the gain control decision, it is allowed to adapt freely all of the time. The under-estimation factor of the main filter can be estimated as $$RatSqG_i = \min\left(\frac{SqGa_i(k)}{SqGb_i(k)}, 1\right)$$

and the double-talk based adaptation gain control decision can be modified as $$\mu_i = \min\left(\frac{|E\{D_i(k)Y_i^*(k)\}|^2}{E\{|D_i(k)|^2\}^2 \times RatSqG_i}, 1\right)\gamma.$$

Typically, the auxiliary filter only affects system performance when its echo path gain surpasses that of the main filter. Furthermore, it only accelerates the adaptation of the main filter because $RatSqG_i$ is limited between 0 and 1.

The acoustic echo cancellation problem is approached based on the assumption that the echo path can be modeled by a linear finite impulse response (FIR) system, which means that the far-end component received by the microphone is the result of the speaker signal transformed by an FIR filter. The AEC filter uses a subband NLMS-based adaptive algorithm to estimate the filter from the speaker and microphone signals in order to remove the far-end component from the microphone signal.

Typically, a residual echo remains in the output of the adaptive filter. A residual echo reduction (RER) filter may be used to reduce the residual echo. For each subband, a one-tap NLMS filter is implemented with the main AEC filter output, $E_i(k)$, as the ideal signal. If the microphone signal, $D_i(k)$, is used as the reference signal, the one-tap filter will converge to $$G_{r,i}(k) = \frac{E\{E_i(k)D_i^*(k)\}}{E\{|D_i(k)|^2\}}.$$

When the microphone signal contains mostly a far-end component, this component should be removed from $E_i(k)$ by the main AEC filter and thus the absolute value of $G_{r,i}(k)$ should be close to 0. On the other hand, when the microphone signal contains mostly near-end component, $E_i(k)$ should approximate $D_i(k)$, and thus $G_{r,i}(k)$ is close to 1. Therefore, by applying $|G_{r,i}(k)|$ as a gain on $E_i(k)$, the residual echo can be greatly attenuated while the near-end speech is mostly intact.

To further protect the near-end speech, the input signal to the one-tap NLMS filter can be changed from $D_i(k)$ to $F_i(k)$, which is a weighted linear combination of $D_i(k)$ and $E_i(k)$ defined as $$F_i(k)=(1-R_{NE,i}(k))D_i(k)+R_{NE,i}(k)E_i(k)$$

where $R_{NE,i}(k)$ is an instantaneous estimate of the near-end energy ratio. With this change, the solution of $G_{r,i}(k)$ becomes $$G_{r,i}(k) = \frac{E\{E_i(k)F_i^*(k)\}}{E\{|F_i(k)|^2\}}.$$

Typically, when $R_{NE,i}(k)$ is close to 1, $F_i(k)$ is effectively $E_i(k)$, and thus $G_{r,i}(k)$ is forced to stay close to 1. On the other hand, when $R_{NE,i}(k)$ is close to 0, $F_i(k)$ becomes $D_i(k)$, and $G_{r,i}(k)$ returns to the previous definition. Therefore, the RER filter preserves the near-end speech better with this modification while achieving similar residual echo reduction performance.

Because $|G_{r,i}(k)|$ is applied as the gain on $E_i(k)$, the adaptation rate of the RER filter affects the quality of output signal significantly. If adaptation is too slow, the on-set near-end speech after echo events can be seriously attenuated, and near-end speech can become ambient as well. On the other hand, if adaptation is too fast, unwanted residual echo can pop up and the background can become watery. To achieve optimal balance, an adaptation step-size control (ASC) is applied to the adaptation gain constant of the RER filter:

$$\mu_{r,i}(k)=ASC_i(k)\gamma_r$$

$$ASC_i(k) = (1-\alpha_{ASC,i})|G_{r,i}(k-1)|^2 + \alpha_{ASC,i}\min\left(\frac{|E_i(k)|^2}{|F_i(k)|^2}, 1\right).$$

$ASC_i(k)$ is decided by the latest estimate of $|G_{r,i}|^2$ plus a one-step look ahead. The frequency-dependent parameter $\alpha_{ASC,i}$, which decides the weight of the one-step look ahead, is defined as $$\alpha_{ASC,i}=1-\exp(-M/(2i)), i=0, 1, \ldots, (M/2)$$

where M is the DFT size. This gives more weight to the one-step look-ahead in the higher frequency subbands because the same number of samples cover more periods in the higher-frequency subbands, and hence the one-step look-ahead there is more reliable. This arrangement results in more flexibility at higher-frequency, which helps preserve high frequency components in the near-end speech.

The divergence control system basically protects the output of the system from rare divergence of the adaptive algorithm and it is based on the conservation of energy theory for each subband of the hands free system. The divergence control system compares, in each subband, the power of the microphone signal, $D_i(k)$, with the power of the output of the adaptive filter $Y_i(k)$. Because energy is being extracted from the microphone signal, the power of the adaptive filter output has to be smaller than or equal to the power of the microphone signal in each subband. If this does not happen, it means that the adaptive subfilter is adding energy to the system and the assumption will be that the adaptive algorithm diverged. If it occurs, the output of the subtraction block, $E_i(k)$, is replaced by the microphone signal $D_i(k)$.

Figure 6:
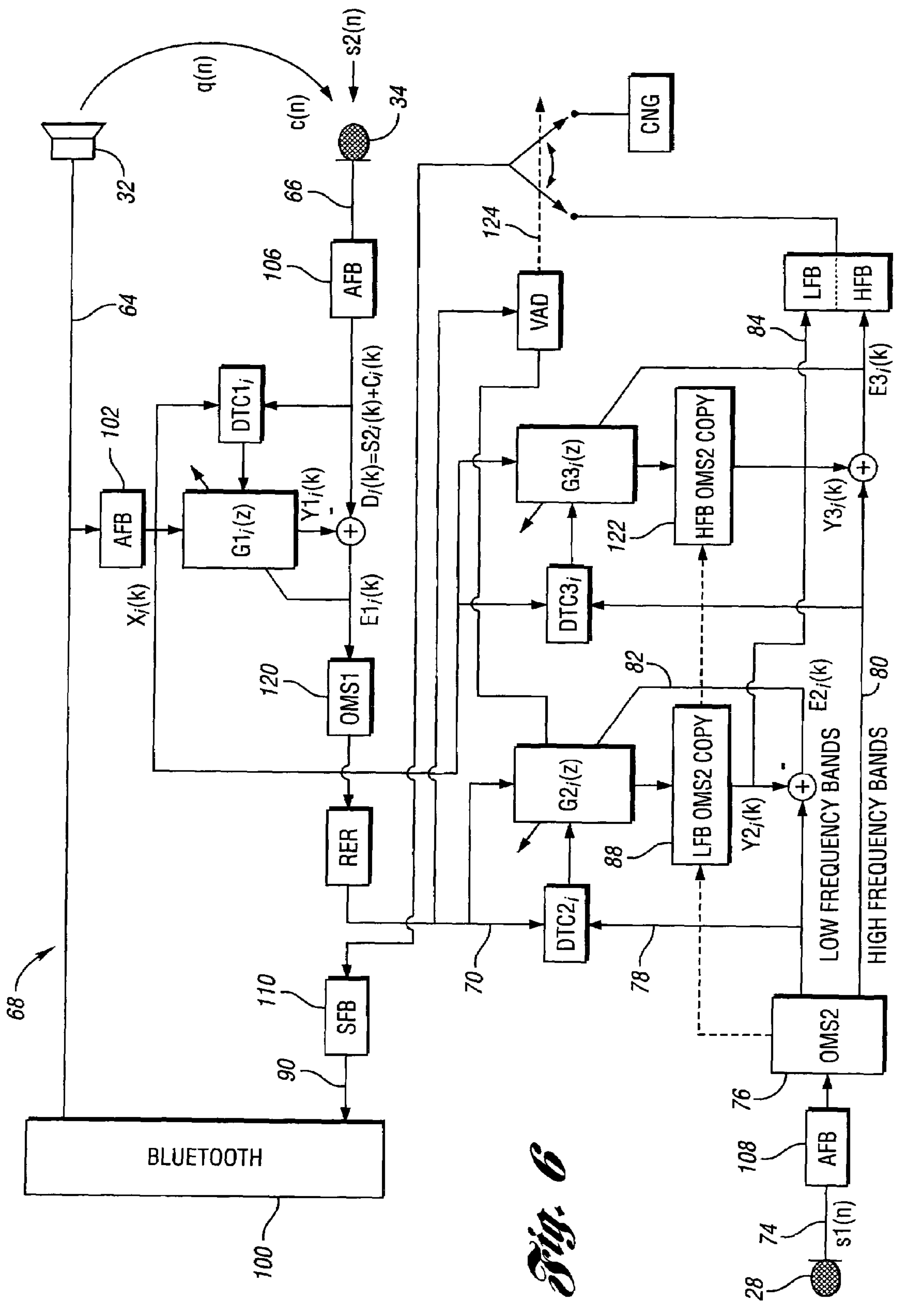
FIG. 6 is a block diagram of an alternative embodiment for noise reduction according to an embodiment of the present invention.

Referring now to FIG. 6, a block diagram of an alternative embodiment for noise reduction according to an embodiment of the present invention is shown. This embodiment includes three modifications over the embodiment of FIG. 3. Some, none, or all of these modifications may be included, depending on the construction and operation of the headset.

First, noise reducer 120 is inserted before the RER in generating echo reducer output 70. Noise reducer 120 reduces the effects of noise which leak into chamber 62, thereby improving isolation of second microphone 34 from the operating environment.

Second, AEC is implemented to reduce the effects of leakage from speaker 32 to first microphone 28. High frequency subband signals $X_i(k)$ and high frequency first signal 80 are used by double talk detector DTC$\mathbf{3}_i$ to restrict conditions under which adaptive filters $G\mathbf{3}_i(z)$ may adapt. The output of adaptive filters $G\mathbf{3}_i(z)$ is filtered by noise reducer 122 to produce signal $Y\mathbf{3}_i(k)$. High frequency output $E\mathbf{3}_i(k)$ is found as the difference between high frequency first signal 80 and $Y\mathbf{3}_i(k)$. The high frequency output $E\mathbf{3}_i(k)$ is used to generate coefficients of adaptive filters $G\mathbf{3}_i(z)$.

Third, a voice active detector (VAD) improves performance in the presence of external talkers. The VAD generates control signal 124 based on the presence of spoken speech in echo reducer output 70. The VAD may also be used to freeze the adaptation of subband adaptive filters $G\mathbf{2}_i(z)$ in order to prevent updating when the wearer's voice is not present. The design and implementation of VADs is well known in the art. Control signal 124 selects either the combined low frequency $Y\mathbf{2}_i(k)$ and high frequency $E\mathbf{3}_i(k)$, representing noise reduced speech, when voice is detected, or the output of the comfort noise generator (CNG) when voice is not detected.

Figure 7:
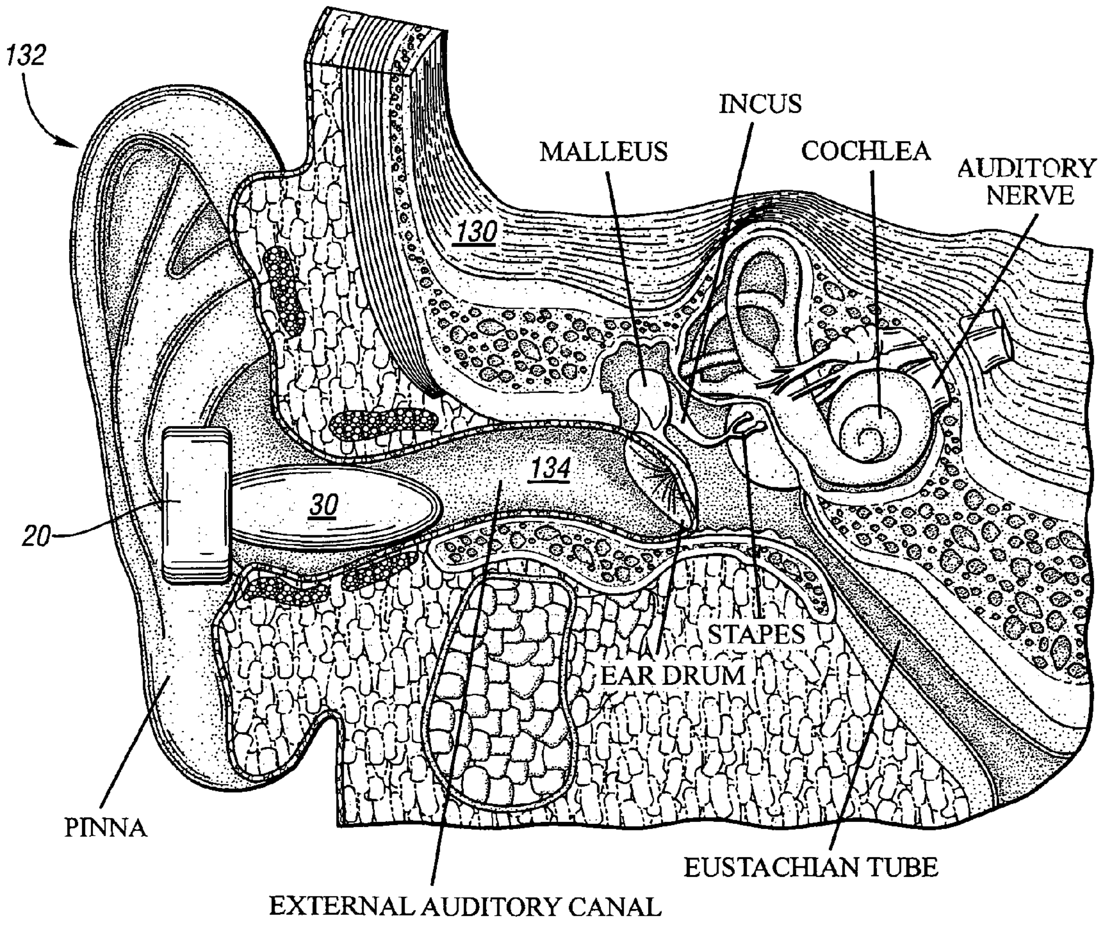
FIG. 7 is a schematic diagram illustrating an earpiece according to an embodiment of the present invention.

Referring now to FIG. 7, a schematic diagram illustrating an earpiece according to an embodiment of the present invention is shown. User 130 has ear 132 shaped to funnel sound into ear canal 134. In a preferred embodiment, headset 20 includes insertion portion 30 which fits at least partially into ear canal 134. When user 130 speaks, sound is conveyed through user 130 into ear canal 134. Locating insertion portion 30 at least partially within ear canal 134 permits reception of conveyed sound while limiting interference by external noise.

FIGS. 8*a*-8*c*, 9*a*-9*c*, and 10*a*-10*c* provide time domain and frequency domain graphs of signals illustrating operation of an embodiment of the present invention. These signals were obtained through simulation using MATLAB® available from The MathWorks, Inc.

Figure 8A:
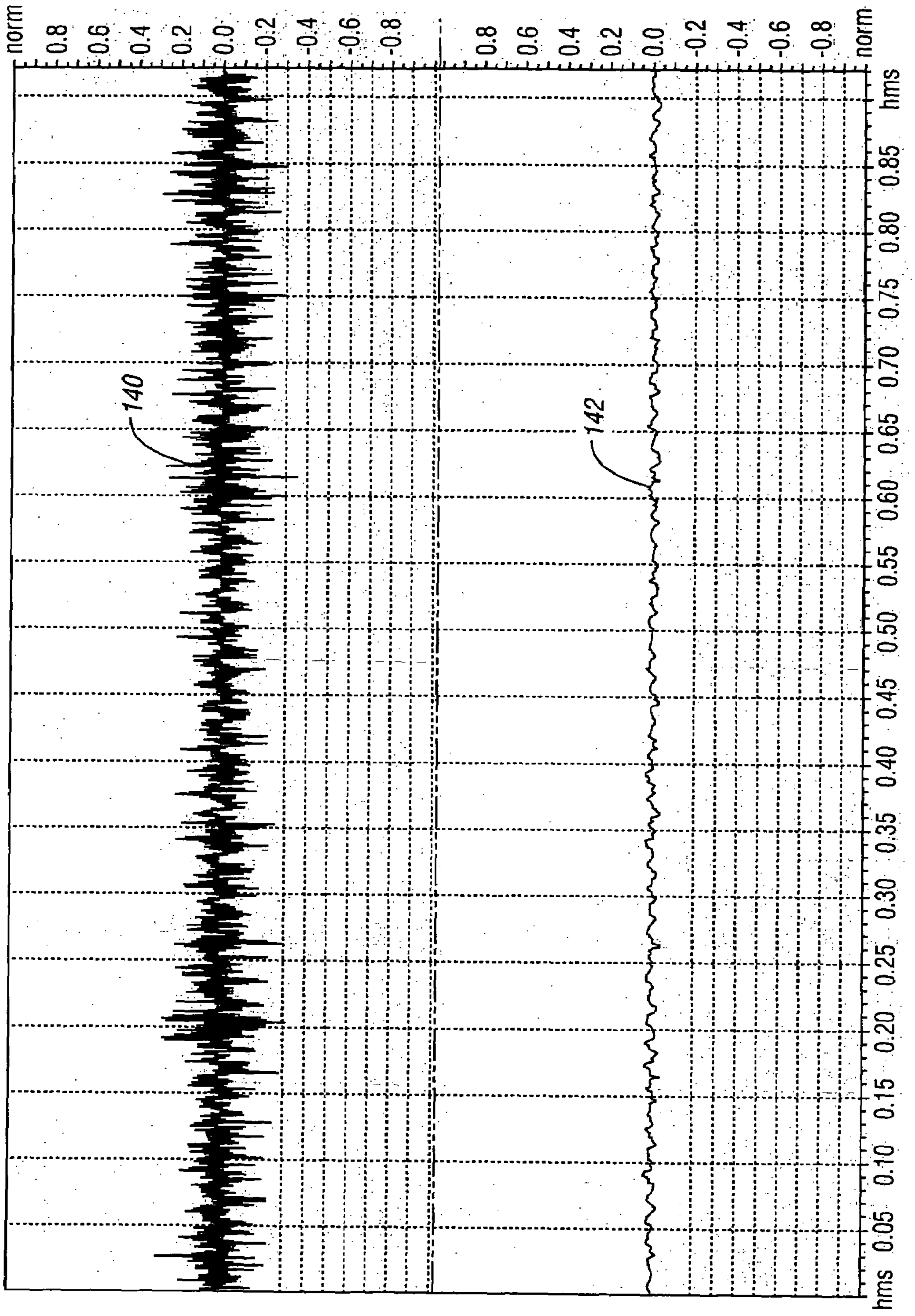
FIG. 8 is a schematic diagram illustrating noise waveforms and corresponding spectrograms of noise inside and outside of a chamber and a system output according to an embodiment of the present invention.
Figure 8B:
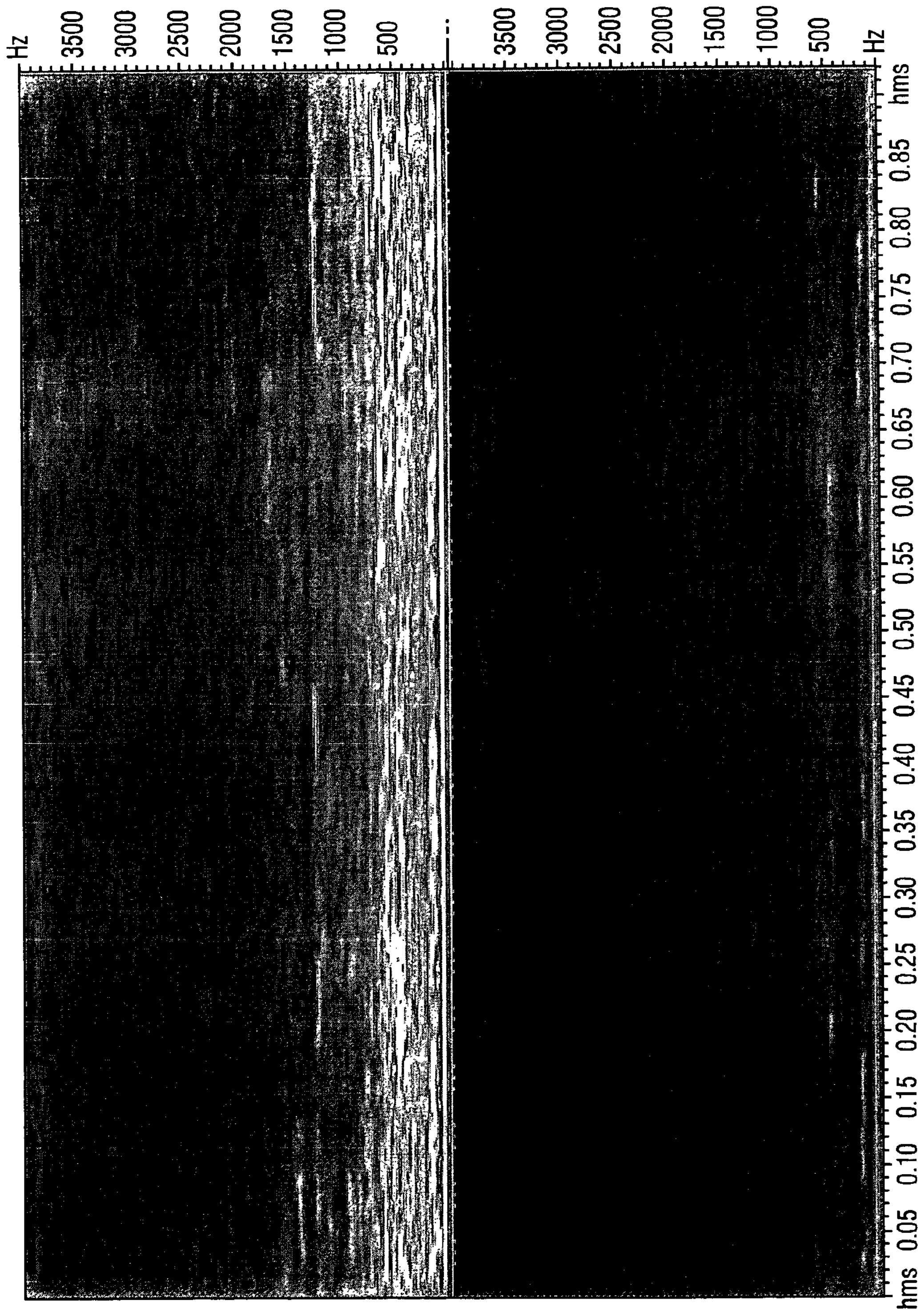
Figure 8C:
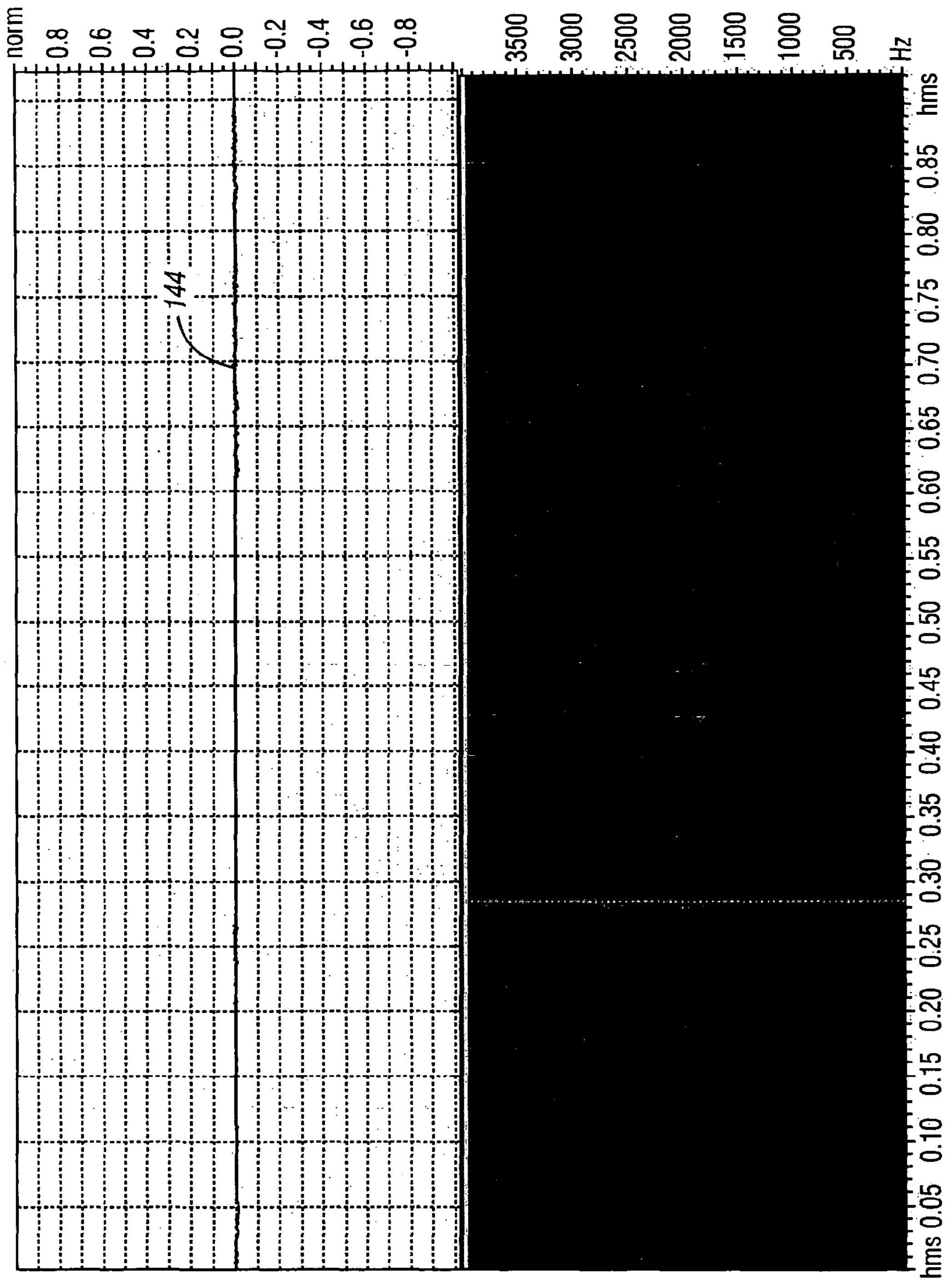

Referring now to FIGS. 8*a*-8*c*, graphs illustrating non-stationary "babble noise" are shown. FIG. 8*a* illustrates noise signal 140 from first microphone 28 and noise signal 142 from second microphone 34. Due to the location of second microphone 34 at least partially within the ear canal of the wearer, sound levels due to external noise are significantly lower in noise signal 142. This is also borne out in the corresponding spectrograms of FIG. 8*b*. The top spectrogram is from first microphone noise signal 140 and the bottom spectrogram is from second microphone noise signal 142. FIG. 8*c* provides the results of processing due to an embodiment of the present invention. Time domain signal 144, shown on top, and the corresponding spectrogram, shown on bottom, illustrate that virtually all noise has been eliminated.

Figure 9A:
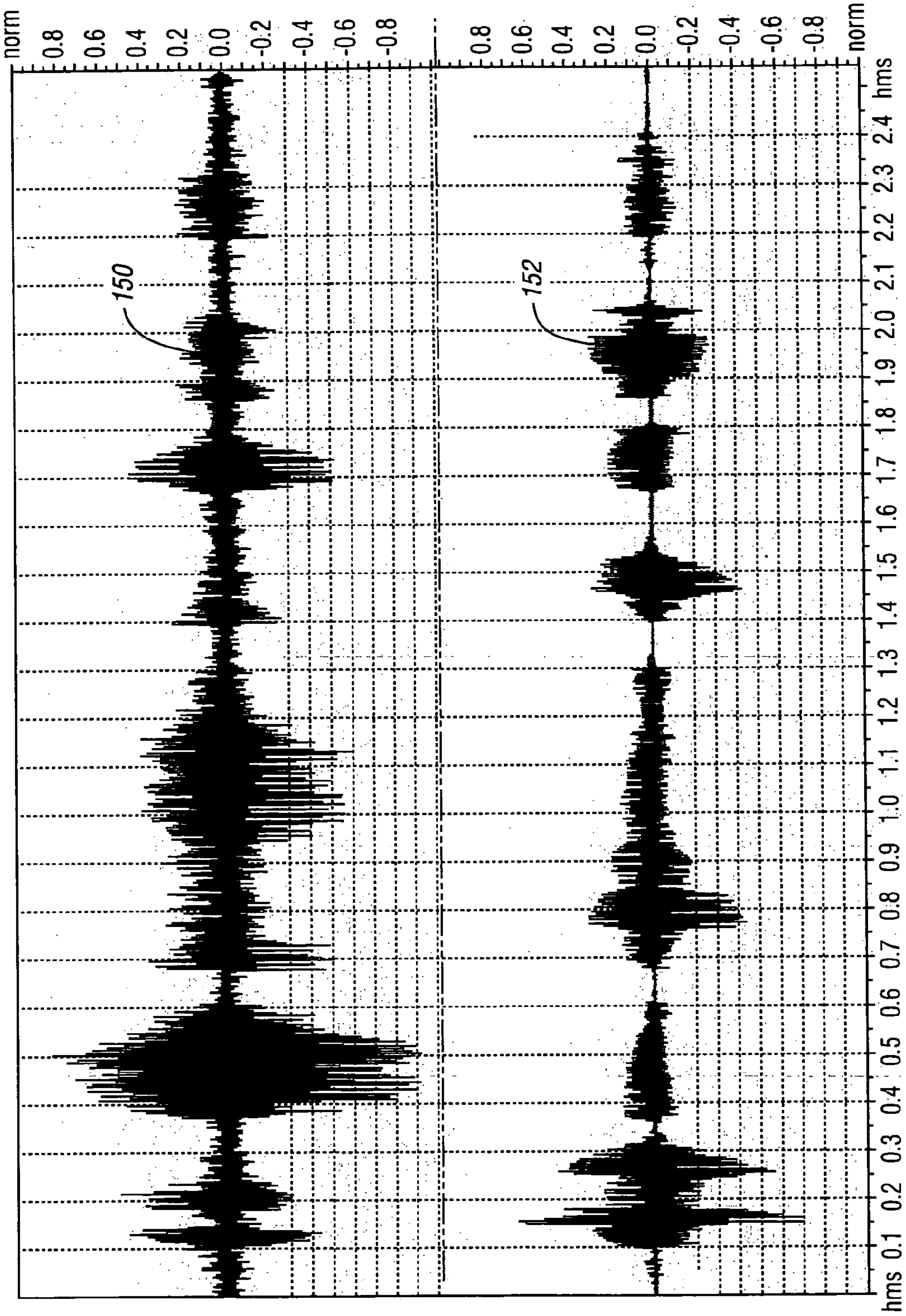
FIG. 9 is a schematic diagram illustrating signal waveforms and spectrograms of low noise speech inside and outside of a chamber and a system output according to an embodiment of the present invention.
Figure 9B:
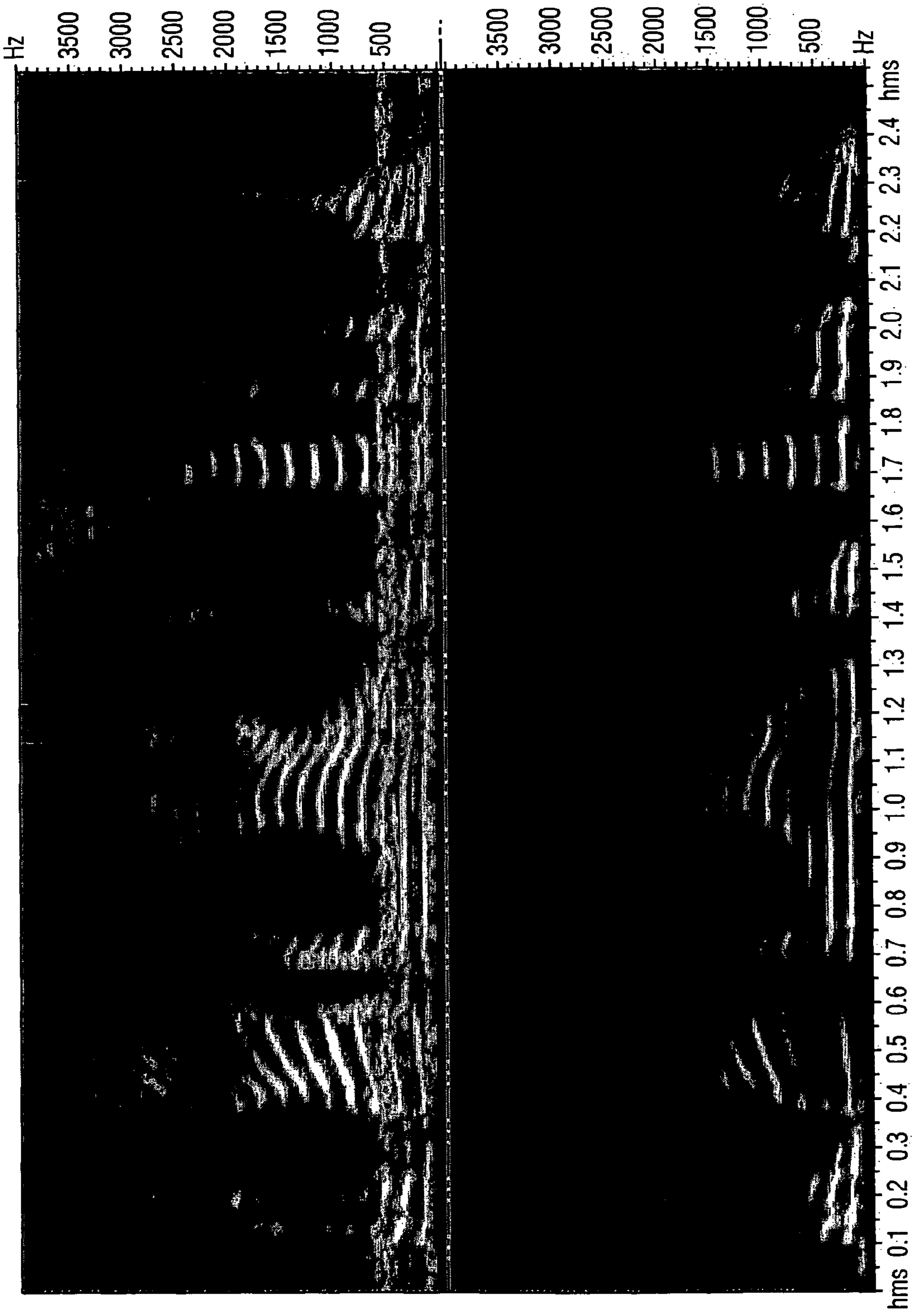
Figure 9C:
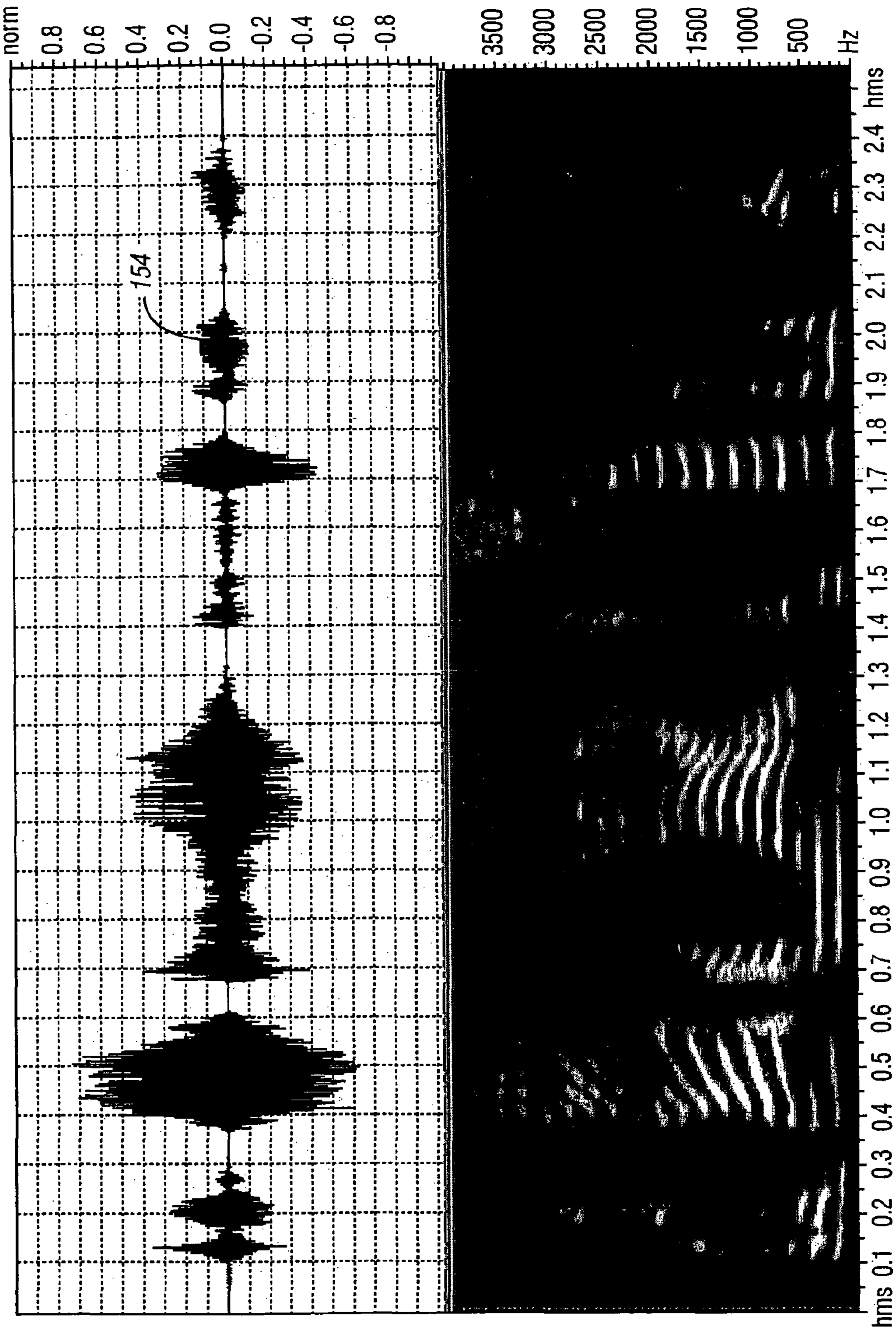

Referring now to FIGS. 9*a*-9*c*, graphs illustrating speech in the presence of low-level non-stationary noise are shown. FIG. 9*a* illustrates speech-plus-noise signal 150 from first microphone 28 and speech-plus-noise signal 152 from second microphone 34. FIG. 9*b* illustrates the corresponding spectrograms, with the top spectrogram from first microphone speech-plus-noise signal 150 and the bottom spectrogram from speech-plus-noise signal 152. FIG. 9*c* provides the results of processing due to an embodiment of the present invention. Time domain signal 154, shown on top, and the corresponding spectrogram, shown on bottom, illustrate a marked decrease in the effect of the noise.

Figure 10A:
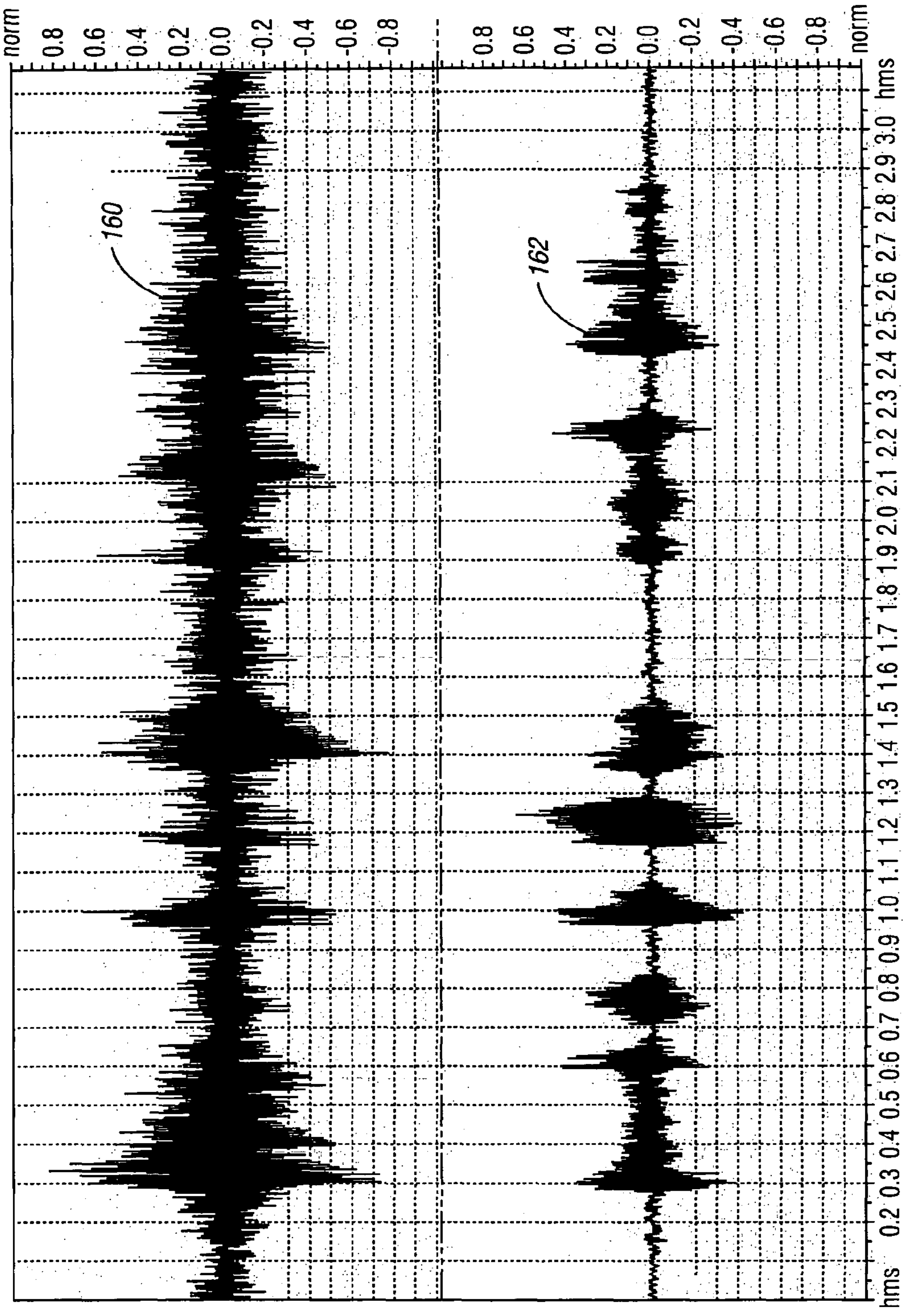
FIG. 10 is a schematic diagram illustrating waveforms and spectrograms of noisy speech inside and outside of a chamber and a system output according to an embodiment of the present invention.
Figure 10B:
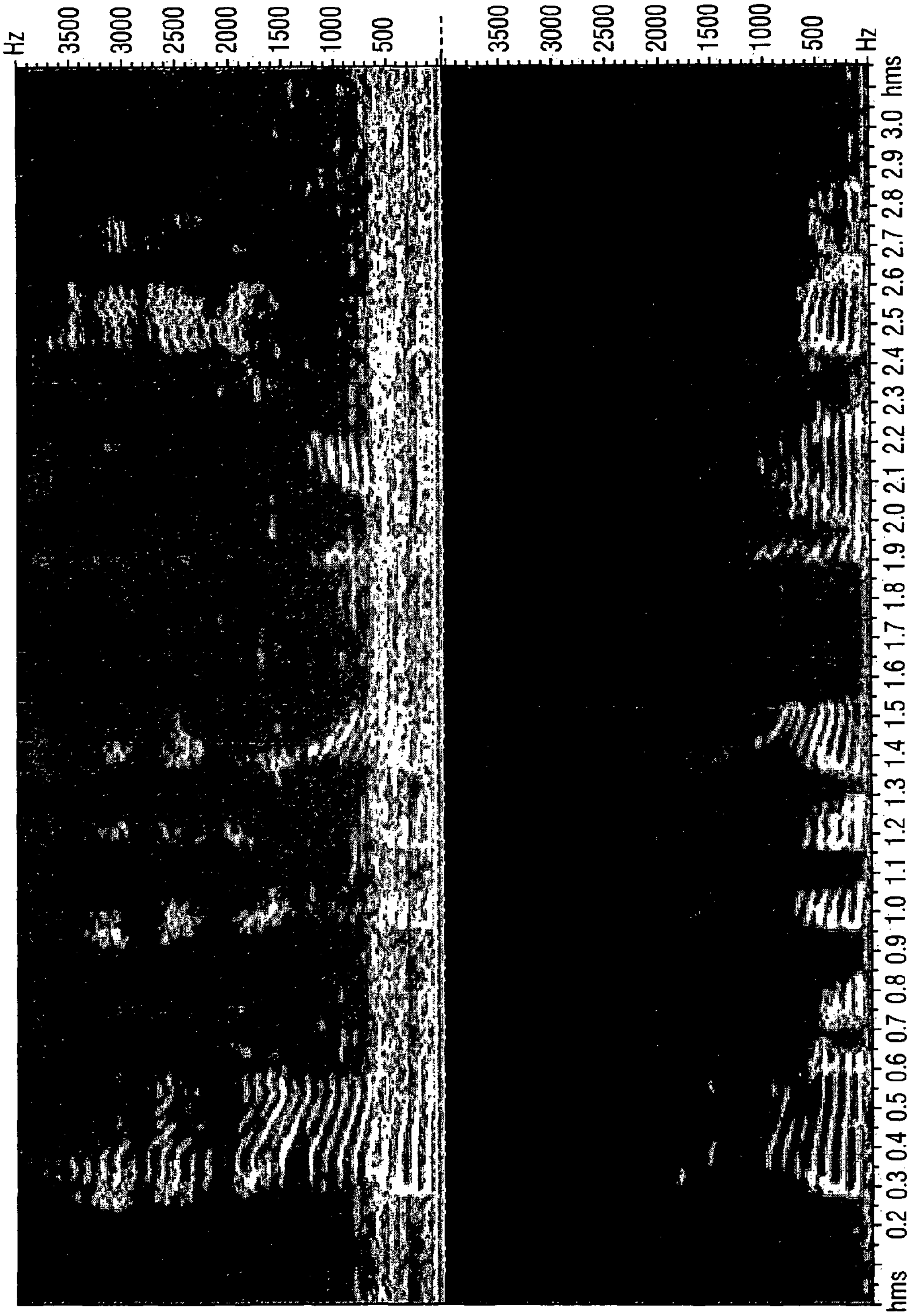
Figure 10C:
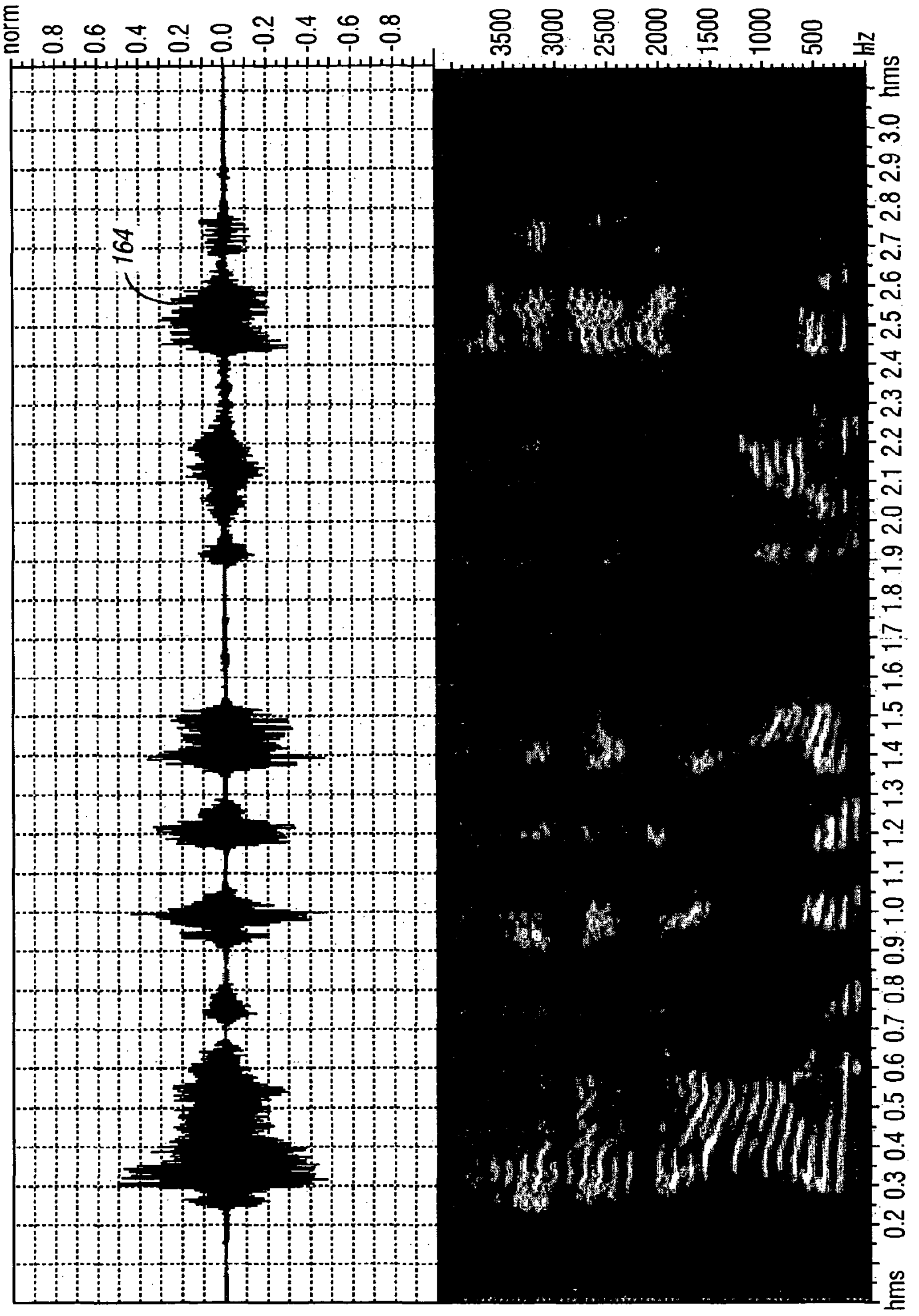

Referring now to FIGS. 10*a*-10*c*, graphs illustrating speech in the presence of high-level non-stationary noise are shown. FIG. 10*a* illustrates speech-plus-noise signal 160 from first microphone 28 and speech-plus-noise signal 162 from second microphone 34. FIG. 10*b* illustrates the corresponding spectrograms, with the top spectrogram from first microphone speech-plus-noise signal 160 and the bottom spectrogram from speech-plus-noise signal 162. FIG. 10*c* provides the results of processing due to an embodiment of the present invention. Time domain signal 164, shown on top, and the corresponding spectrogram, shown on bottom, illustrate a marked decrease in the effect of the noise. As seen in FIG. 10*c*, even in the presence of relatively severe noise, the present invention can extract a clean speech signal.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A system comprising:
- an ear portion forming a chamber with at least a portion of an ear, the chamber reducing ambient noise from outside the chamber;
- a first microphone outside the chamber positioned to pick up vocal sound from a wearer of the system, the first microphone generating a first signal;
- a speaker providing sound to the chamber;
- a second microphone disposed within the chamber generating a second signal;
- an echo reducer reducing the effects of the speaker signal in the second signal; and
- a dynamic equalizer adjusting the frequency spectrum of the second signal based on the first signal to produce a filtered signal.

2. The system of claim 1 further comprising a first noise reducer reducing noise in the first signal.

3. The system of claim 1 wherein an output signal is produced by combining low frequency output based on the filtered signal with high frequency output based on the first signal.

4. The system of claim 3 wherein the echo reducer is a first echo reducer, the system further comprising a second echo reducer reducing the effects of the speaker signal in the high frequency output.

5. The system of claim 1 further comprising a double talk detector.

6. The system of claim 1 further comprising:
- a first analysis filter in communication with the first microphone, the first analysis filter generating a first analysis filter output comprising a frequency domain representation of the first signal;
- a second analysis filter in communication with the second microphone, the second analysis filter generating a second analysis filter output comprising a frequency domain representation of the second signal; and
- a synthesis filter generating a time domain representation of the filtered signal.

7. A method of generating a reduced noise vocal signal in a system having a first microphone and an earpiece, the earpiece forming a chamber with an ear when the earpiece is in contact with the ear, the earpiece including a speaker and a second microphone, the second microphone operative to sense sound in the chamber, the method comprising:
- decomposing output of the first microphone into a first subbanded signal;
- decomposing output of the second microphone into a second subbanded signal;
- generating an equalized signal by equalizing the second subbanded signal based on the first subbanded signal; and
- producing the reduced noise vocal signal based on the equalized signal and on the first subbanded signal.

8. The method of claim 7 wherein the reduced noise vocal signal is based on low frequency components of the equalized signal and on high frequency components of the first subbanded signal.

9. The method of claim 8 further comprising canceling echos in the high frequency components of the first subbanded signal.

10. The method of claim 7 further comprising canceling echos in the second subbanded signal prior to generating the equalized signal.

11. The method of claim 10 wherein canceling echos is based on a subbanded input to the speaker.

12. The method of claim 7 wherein the equalized signal is generated based on a plurality of low frequency subbands of the first subbanded signal.

13. The method of claim 7 further comprising reducing noise in the equalized signal.

14. The method of claim 7 further comprising reducing noise in the first subbanded signal.

15. A method of generating a reduced noise vocal signal in a system having a first microphone and an earpiece, the earpiece forming a chamber with an ear when the earpiece is in contact with the ear, the earpiece including a speaker and a second microphone, the second microphone operative to sense sound inside the chamber to produce a second signal and the first microphone operative to sense sound outside the chamber to produce a first signal, the method comprising:
- filtering noise from the first signal to produce a first filtered signal;
- generating an equalized signal by equalizing the second signal based on the first filtered signal;
- filtering noise from the equalized signal to produce a second filtered signal; and
- generating the reduced noise vocal signal based on the first filtered signal and the second filtered signal.

16. The method of claim 15 further comprising generating a first low frequency signal and a first high frequency signal, the first low frequency signal having high frequency components of the first filtered signal removed and the first high frequency signal having low frequency components of the first filtered signal removed.

17. The method of claim 16 wherein the equalized signal is based on the first low frequency signal.

18. The method of claim 16 wherein the equalized signal is based on a difference between the first low frequency signal and the second filtered signal.

19. The method of claim 16 wherein the reduced noise vocal signal is generated by combining the second filtered signal and the first high frequency signal.

20. The method of claim 16 further comprising canceling echos in the first high frequency signal.

21. The method of claim 15 further comprising canceling echos in the second signal.

22. The method of claim 15 further comprising using voice detection to selectively enable outputting the reduced noise vocal signal.

23. The method of claim 15 further comprising reducing noise in the second signal prior to equalizing the second signal.

24. A system for generating a reduced noise vocal signal based on speech spoken by a user, the user using an ear portion forming a chamber with at least a portion of an ear of the user, the chamber reducing ambient noise from outside the chamber, the chamber including a speaker providing sound to the ear of the user, the user also using a first microphone outside the chamber positioned to pick up the speech spoken by the user, the first microphone generating a first signal based on the speech spoken by the user, the system comprising:

a second microphone disposed within the chamber generating a second signal, the second signal based on the speech spoken by the user; and audio processing circuitry in communication with the first microphone and the second microphone, the audio processing circuitry operative to generate the reduced noise vocal signal by generating an equalized signal by equalizing the second signal based on the first signal, and producing the reduced noise vocal signal based on the equalized signal and on the first signal.

* * * * *